United States Patent
Rao et al.

(10) Patent No.: US 7,112,424 B2
(45) Date of Patent: Sep. 26, 2006

(54) PROCESS FOR THE PREPARATION OF PROTEIN HYDROLYSATE FROM LEGUMES

(75) Inventors: Appu Rao Gopala Rao Appu Rao, Mysore (IN); Karadka Govindaraju, Mysore (IN); Ramaswamy Harendranath, Mysore (IN); Johny Joseph, Mysore (IN); Vishweshwariah Prakash, Mysore (IN); Cheruppanpullil Radha, Mysore (IN); Mysore Cheeluvaraya Shamanthaka Sastry, Mysore (IN); Sridevi Annapurna Singh, Mysore (IN)

(73) Assignee: Council of Scientific and Industrial Research, (IN)

( * ) Notice: Subject to any disclaimer, the term of this patent is extended or adjusted under 35 U.S.C. 154(b) by 0 days.

(21) Appl. No.: 09/811,766

(22) Filed: Mar. 19, 2001

(65) Prior Publication Data

US 2002/0132287 A1  Sep. 19, 2002

(51) Int. Cl.
*C12N 9/00* (2006.01)
(52) U.S. Cl. .................................... 435/183
(58) Field of Classification Search ............... 435/219, 435/223, 183
See application file for complete search history.

(56) References Cited

U.S. PATENT DOCUMENTS

| 4,431,629 | A | * | 2/1984 | Olsen |
| 4,757,007 | A | * | 7/1988 | Satoh et al. |
| 5,854,050 | A | * | 12/1998 | Dalboge et al. |
| 6,007,851 | A | * | 12/1999 | Schoenmaker et al. |
| 6,251,443 | B1 | * | 6/2001 | Chigurupati et al. |
| 6,313,273 | B1 | * | 11/2001 | Thomas et al. |
| 6,372,282 | B1 | * | 4/2002 | Edens et al. |

FOREIGN PATENT DOCUMENTS

EP   148600   *  7/1985

* cited by examiner

*Primary Examiner*—Michael Meller
(74) *Attorney, Agent, or Firm*—Butzel Long

(57) ABSTRACT

The present invention provides a process for the preparation of protein hydrolysate from soy flour, which comprises preparing an aqueous slurry of defatted soy flour having 6–12% w/v of solid content, hydrolyzing the slurry using fungal protease at pH 7–8 and temperature 43±5° C. to get 20–40% degree of hydrolysis (DH), further hydrolyzing using papain at a temperature of 53±5° C. under stirring till completion of hydrolysis to 30–45% DH, inactivating residual enzyme in a known manner, and separating the solids and drying the clarified supernatant thus obtained to get protein hydrolysate.

14 Claims, No Drawings

PROCESS FOR THE PREPARATION OF PROTEIN HYDROLYSATE FROM LEGUMES

FIELD OF THE INVENTION

The present invention relates to a process for the preparation of protein hydrolysate from soy flour using fungal protease. Particularly, the present invention relates to a process for the preparation of protein hydrolysate from defatted soy flour using fungal protease obtained from *Aspergillus* sp.

BACKGROUND OF THE INVENTION

Presently about 6.8 M tons of soybean is produced in India and extracted for oil and the solvent extracted flour is exported for feed purposes. By providing additional facilities for the hygienic processing of soybean in the solvent extraction units, it is possible to obtain edible grade defatted flour having the desired functional characteristics. After the recovery of oil, 4.9 M tons of soy flour is available for utilization in India. As a by-product of edible oil production, oilseed proteins are a potentially important source of human dietary protein throughout the world. Following oil removal, the protein present in the defatted cakes is heat-denatured and therefore directly un-extractable. Hence, proteolysis is an attractive approach for recovering the protein from cake in soluble form and affords a high protein preparation suitable for protein fortification of a wide variety of foods. A small portion of total soybean produced also finds use for different edible grade flours, protein isolate and texturized products and popularity of these products are greatly picking up globally. Soybean is an excellent source of protein, which contains about 40% protein. New manufacturing techniques for high quality soybean foods have been developed by lowering or destroying of the anti-nutritional factors like trypsin inhibitors.

U.S. Pat. No. 5,180,597 sets forth a process for hydrolyzed vegetable protein with enhanced flavor, which contains no detectable level of monochlorodihydroxypropanol. In the above reference, wheat gluten is hydrolyzed using Prozyme 6 (a fungal protease) at a temperature of 40–50° C., pH 6.5–7.0, with an enzyme concentration of 0.1–2.0% of substrate for a time period of 4 h. The hydrolyzed protein is treated with gaseous HCl for deamidation before the addition of acid for inactivating the enzyme. The drawback in such hydrolysis is that it is likely to lead to racemisation of amino acids and the addition of acid increases the salt content in the product.

Reference may be made to Ernster, J. H. (1991), U.S. Pat. No. 5,077,062, Excelpro Inc., Los Angeles, Calif. USA, wherein a low sodium, low mono sodium glutamate soy hydrolysate that is prepared from soy material such as soy flour, soy meal or soy grits using fungal protease in water is described. The hydrolysis is conducted in the absence of acid or base at 90° C. for 2 h. After deactivating the enzyme and de-watering the mixture the resulting hydrolysate contains between 45 and 55 wt. % enzymatically hydrolyzed soy based protein with an average molecular weight of 670,000±50,000. The fungal protease used is different from the enzyme used in the present invention. Such single enzyme systems are likely to result in bitter peptides and the process is energy intensive due to the high temperature (90° C.) used.

Reference may be made to Satoh et al., (1988) U.S. Pat. No. 4,757,007, Nisshin Oil Mills, and Tokyo, Japan wherein the method describes preparation of two hydrolyzed products using a protease from soy protein. The soy protein is hydrolyzed with papain or pepsin after precipitating with alcohol. The drawback of the process is it involves the separation of the mixture of hydrolyzed products. Hydrolysis is carried out using papain or pepsin. Acidification is carried out to bring down the pH to 2.5–5.0 to separate the two kinds of hydrolysates, which could lead to increase in salt content.

Reference may be made to Cipollo, K. L. and Wagner, T. J., (1987) European Patent No. 0148600 B 1, Ralston Purina Co., wherein the described process relates to the preparation of hydrolyzed protein from protein isolate after jet cooking or dynamic heating at 104° C. for a few seconds and later cooled in a vacuum chamber before hydrolysis using bromelain. The protein was precipitated at its isoelectric point from an aqueous extract of the material before the hydrolysis. The drawback of the process is the starting material protein isolate which is expensive. The process is a multi-step process, energy intensive. The process further needs machines like the jet cooker and a vacuum chamber.

Reference may be made to Parker, D. M. and Pawlett, D. (1987) European Patent No. 0223560 A2, Imperial Biotechnology Ltd., wherein the method describes the separation of protein hydrolysates with meat and cheese flavor, from proteinaceous feed stocks (e.g. containing soybean, gluten, whey, casein, hemoglobin, yeast, cereal or microbial proteins) by stepwise hydrolysis using an endopeptidase followed by amino peptidase from Streptococcus lactus. The drawback of the process is it is a multi-step process.

Reference may be made to Lee, (1986) European Patent No. 0087246 B1, Staffer Chemical Co. wherein a process for the hydrolysis of soybeans, wheat gluten and cotton seeds using fungal protease from *Aspergillus* and pancreatin (trypsin, chymotrypsin A, B and C, elastase and carboxypeptidase A and B) is described. Activated charcoal is used to treat the hydrolysate, which is used for nutritional improvement. The draw back of the process is that it involves many more steps.

Reference may be made to a Boyce, C. O. L. et al. (1986) European Patent No. 0187048 A2, NOVO Industries A/S, wherein a process is described for the preparation of soy protein hydrolysate with 0.25 to 2.5% degree of hydrolysis (DH) using microbial rennet (*Mucor miehei*) and to be used as an egg white substitute. The enzyme used in this process is different and involves a low degree of hydrolysis of soy protein.

Reference may be made to Olsen, H. A. S. (1981), United Kingdom Patent No. 2053228A, wherein a process for the production of soy protein hydrolysate from partially defatted soy material by hydrolysis with proteolytic enzyme. The drawback of the process is that due to partial defatting soy flour, left over oil comes in contact with protein phase, which could lead to off-flavors.

Reference may be made to Olsen, H. S. (1981) U.S. Pat. No. 4,324,805, wherein method described for producing soy protein hydrolysate and oil from partially defatted soy material by hydrolysis with proteolytic enzyme. The soy flour is partially defatted by water washing at pH 3.5–4.5 and later hydrolyzed using water and a base to increase the pH. The degree of hydrolysis (DH) is in the range of 8–12%. Oil is recovered from the wash water. Alcalase is the enzyme used. The drawback of the process is that it is a multi-step process and, due to partial defatting of soy flour, left over oil comes in contact with protein phase which could lead to off-flavors. Enzyme inactivation is done by addition of acid, which is likely to lead to increased salt content in the product.

Reference may be made to Sherba and Steiger (1972), U.S. Pat. No. 3,640,725, wherein enzymatic hydrolysis process for production of soy protein hydrolysates is described. The soy seeds are comminuted and heated at 90–140° C. Protease (fungal and bacterial) is added at 25–75° C. The fiber is separated and slurry has two phases—oil and aqueous phase. Aqueous phase is brought to pH 4.5 to precipitate the protein, which is then concentrated. The starting material is not defatted and hence the residual oil could come in contact with the aqueous phase, which could lead to off-flavors.

Reference may be made to Gunther, R. C. (1972) Canadian Patent No. 905742, wherein soy protein hydrolysate is modified with pepsin to yield a product, which, in presence of water and sugar, whips at a rapid rate to produce aerated products of low density.

Reference may be made to Tsumura, K. et al, (1997) European Patent No. 0797928 A1, wherein a process for the manufacture of a soy protein hydrolysate with a protease used selectively to decompose glycinin at a pH of 1.5–2.5. The pH used in the process is very low and therefore differs from the pH used in the present invention. Further, the aim of the process is to achieve a low glycinin content, which is not the case in the present invention.

Reference may be made to a published paper entitled "Industrial Production and Application of Soluble Enzymatic Hydrolysate of Soy Protein", by Olsen, H. S., Adler Nissen, J. (1979), Process Biochemistry, 14(7), 6,8, 10–11, wherein a method for the preparation of soy protein hydrolysate from soy flakes washed at pH 4.5 followed by hydrolysis using alcalase is described. The solubility of the substrate is low at the acidic pH which is likely to result in low yields. The enzyme used is different from the enzyme used in the present invention.

OBJECTS OF THE INVENTION

The main object of the present invention is to provide a process for the preparation of protein hydrolysate from soy flour using microbial protease.

Another object of the present invention is to provide a process for the preparation of protein hydrolysate from defatted soy flour using *Aspergillus* sp.

Still another object of the present invention is to provide a process for preparing protein hydrolysate by double enzyme hydrolysis using proteolytic enzymes.

Yet another object of the present invention is to decrease the bitterness in the hydrolysate to the extent that the threshold perception of bitterness is greater than 2 g %.

One more object of the present invention is to provide a process for the preparation of protein hydrolysates with a low mineral content.

One another object of the present invention is to provide a process for the preparation of protein hydrolysate in higher yield and with a specified degree of hydrolysis from the raw material taken.

SUMMARY OF THE INVENTION

Accordingly, the present invention provides a process for the preparation of protein hydrolysate from soy flour, which comprises preparing an aqueous slurry of defatted soy flour having 6–12% w/v of solid content, hydrolyzing the slurry using fungal protease at pH 7–8 and a temperature of 43±5° C. to get 20–40% DH, further hydrolyzing using papain at a temperature of 53±5° C. under stirring till completion of hydrolysis to 30–45% DH, inactivating the residual enzyme in a known manner, and separating the solids and drying the clarified supernatant thus obtained to get protein hydrolysate.

DETAILED DESCRIPTION OF THE INVENTION

Accordingly, the present invention provides a process for the preparation of protein hydrolysate from soy flour using fungal protease, the process comprising: preparing an aqueous slurry of defatted soy flour having 6–12% w/v of solid content; hydrolyzing the slurry using fungal protease at pH 7–8 and a temperature of 43±5° C. to get 20–40% degree of hydrolysis (DH); further hydrolyzing using papain at a temperature of 53±5°C. under stirring till 30–45% DH is obtained; inactivating residual enzyme in a known manner; and separating the solids and drying the clarified supernatant thus obtained to get protein hydrolysate.

In an embodiment of the present invention, the solid content in the slurry ranges from 8–12% w/v.

In another embodiment of the present invention, the fungal protease is obtained from *Aspergillus* sp.

In still another embodiment of the present invention, the *Aspergillus* is selected from the group comprising *A. flavus, A. japanicus, A. niger* and *A. awamori*.

In yet another embodiment of the present invention, protein hydrolysate is obtained by double enzyme hydrolysis.

In one more embodiment of the present invention, protein hydrolysate is obtained by hydrolyzing the slurry with proteolytic enzyme.

In one another embodiment of the present invention, the fungal protease used ranges from 0.4 to 0.5% w/w of the soy flour.

In an embodiment of the present invention, protease hydrolysis is carried out at a pH of 7.2 to 7.6.

In another embodiment of the present invention, the amount of papain used ranges from 0.4 to 0.5% w/w of the soy flour.

In still another embodiment of the present invention, the hydrolysate produced has decreased bitterness.

In yet another embodiment of the present invention, the threshold perception of bitterness is greater than 2 g %.

In one more embodiment of the present invention, the protein hydrolysate produced has low mineral content.

In one other embodiment of the present invention, a high yield of protein hydrolysate with 35 to 45% degree of hydrolysis is obtained from the raw material taken.

In an embodiment of the present invention, the soy protein hydrolysate obtained has creamy color and a yield of 60–67.0% (on protein basis).

In another embodiment of the present invention, soy protein hydrolysate has 9.4% moisture, 10.5–11.0% nitrogen and 35–45% degree of hydrolysis.

In still another embodiment of the present invention, the soy protein hydrolysate obtained has 20–23 trypsin inhibitor units/mg activity, 95 to 98% Nitrogen Solubility Index, 0.6 to 1.0% of salt content and 2 to 2.2% bitterness recognition threshold.

In yet another embodiment of the present invention, lipoxygenase and urease activities of the protein hydrolysate were not detectable.

In one more embodiment of the present invention, the amino acid composition of the protein hydrolysate is similar to the amino acid makeup of the starting material.

In one another embodiment of the present invention, the protein hydrolysate is creamy in color.

The present invention also provides a protein hydrolysate having 60 to 67% protein hydrolysate on protein basis.

In another embodiment of the present invention, the protein hydrolysate has 9.4% moisture, 10.5 to 11% nitrogen, and 35 to 45% degree of hydrolysis.

In still another embodiment of the present invention, the protein hydrolysate has 20 to 23 trypsin inhibitor units/mg activity, 95 to 98% Nitrogen Solubility Index, 0.6 to 1.0% salt content and 2 to 2.2% bitterness recognition threshold.

In yet another embodiment of the present invention, the protein hydrolysate has undetectable lipoxtgenase and urease activities.

In one more embodiment of the present invention, the protein hydrolysate has similar acid makeup as that of the starting material.

The process steps involved in the preparation of protein hydrolysate are described below:

(1) Defatted soy flour: Soybean flour is derived from clean round beans. The cleaned beans are passed through a cracking process; the bean fragments are graded on sieves and aspirate system. The cleaned, cracked meat is passed through a conditioner cooker and flaked. This is subjected to solvent extraction process. The extracted flakes were desolventized and ground to 100 mesh. The specification for soy flour consists of (a) Moisture % by mass, max. 9% (b) Protein on dry basis % by mass, min. 48%, (c) total ash on dry basis, % by nmass max. 7.2%, (d) acid insoluble ash on dry basis % by mass max. 0.4%, (e) fat on dry basis % by mass, 1.5% (f) crude fiber on dry basis % by mass max. 4.2%, (g) Aflatoxin max. 30 ppb (h) residual solvent 170 ppm, (I) total bacterial count per gram 50,000, (j) Coliform bacteria per gram>10 and (k) Salmonella bacteria–nil.

(2) Fungal enzyme: Commercially available food grade enzyme protease P "amano" 6 from M/s Amano Pharmaceutical Co. Ltd., 2–7, 1-Chome, Nishiki, Nak-ku, Nagoya, 460, Japan, having not less than 60,000 U/g proteolytic activity. The specification of the plant thiol protease papain is to obtain commercially available food grade enzyme having proteolytic activity not less than 2,000 Tyrosine Units (TU)/mg proteolytic activity.

(3) Measurement of Degree of Hydrolysis (DH): Trinitrobenzenesulphonic acid (TNBS) procedure, is an accurate, reproducible and generally applicable procedure for determining the degree of hydrolysis of food protein hydrolysates. The protein hydrolysate is dissolved/dispersed in hot 1% sodium dodecyl sulphate to a concentration of $0.25-2.5 \times 10^{-3}$ amino equivalents/L. A sample solution (0.25 ml) is mixed with 2 ml of 0.2125 M sodium phosphate buffer (pH 8.2) and 2 ml of 0.1% TNBS, followed by incubation in the dark for 60 min at 50° C. The reaction is quenched by adding 4 ml of 0.1N hydrochloric acid (HCl) and the absorbance is read at 340 nm. A 1.5 mM L-leucine solution is used as the standard. Transformation of the measured leucine amino equivalents to a degree of hydrolysis is carried out by means of a standard curve for each particular protein substrate. (Adler-Nissen, J. (1979) J. Agr. Food Chem. 27,6, 1256–1262)

Defatted soy bean flour was dispersed in water with a suitable solvent to solute ratio and the pH of the dispersion was adjusted using 6N sodium hydroxide or 6N hydrochloric acid. This was stirred for a few minutes with a mechanical stirrer and then the temperature was raised to 40 to 45° C. At this stage 0.4 to 0.5% of fungal enzyme on the basis of soy flour was added and stirring continued for 2 hours. At the end of stipulated time, the temperature of the slurry was raised 50 to 55° C. To this, 0.4 to 0.5% of papain on the basis of soy flour was added and stirring continued for 1 to 2 hours. At the end of the above time interval, the temperature of the slurry was raised 90 to 95° C. for 5 to 10 minutes. The slurry was cooled to room temperature and the insoluble carbohydrate-rich fraction was removed by centrifugation. The clarified protein hydrolysate was spray dried to obtain protein hydrolysate.

The following examples are given by way of illustration of the present invention and therefore should not be construed to limit the scope of the present invention.

EXAMPLE 1

Twenty-five grams of defatted soy flour were dispersed in 250 ml of water and the pH of the dispersion was adjusted to 7.2 using 6N sodium hydroxide solution. It was stirred for 20 min with a mechanical stirrer and the temperature was raised to 40° C. by heating. At this stage, 125 mg of fungal protease was added and stirring continued for 2 hours. At the end of 2 hours, the temperature was raised to 50° C. by heating and the second enzyme, papain (125 mg), was added and stirred for 1 hour. After the hydrolysis, the resultant solution was boiled for 10 min for enzyme inactivation. The slurry was centrifuged using a basket centrifuge. The clear solution was lyophilised. The yield was 65% on protein basis and the degree of hydrolysis by TNBS method was found to be 43%.

EXAMPLE 2

Fifty grams of soy flour were dispersed in 500 ml of water and the pH of the dispersion was adjusted to 7.3. It was stirred for 20 min with a mechanical stirrer and the temperature was raised to 43° C. At this stage 250 mg of fungal protease was added and stirring was continued for 1.5 hours. At the end of 2 hours the temperature was raised to 53° C. and the second enzyme papain (250 mg) was added and stirred for 1 hours. After the hydrolysis the hydrolysate was boiled for 15 min. for enzyme inactivation and was centrifuged. The clear solution was lyophilised. The yield was 68.0% on protein basis and degree of hydrolysis by TNBS method was 39%.

EXAMPLE 3

One hundred grams of defatted soybean flour was dispersed in 1 L of water and the pH of the dispersion was adjusted to 7.6. It was stirred for 20 min with a mechanical stirrer and then temperature was raised to 45° C. At this stage 500 mg of fungal protease was added and stirring continued for 2 hours. At the end of 2 hours the temperature was raised to 55° C. and the second enzyme papain 500 mg was added and was stirred for 1.5 hours. After the hydrolysis the hydrolysate was boiled for 10 minutes for enzyme inactivation and was centrifuged. The clear solution was spray dried. The yield was 70% on protein basis and degree of hydrolysis by TNBS method was 38%.

EXAMPLE 4

One kg of soy flour was dispersed in 10 L of water and the pH of the dispersion was adjusted to 7.6. It was kept stirring for 15 minutes with a mechanical stirrer and then the temperature was raised to 45° C. At this stage, 5 g of fungal protease was added and stirring continued for 2 hours. At the end of 2 hours, the slurry temperature was raised to 55° C. and the second enzyme papain (5 g) was added and stirred for 1.5 hours. After hydrolysis, the hydrolysate was boiled for 15 minutes for enzyme inactivation and was centrifuged in a basket centrifuge. The clear solution was spray dried. The degree of hydrolysis was found to be 38% and the yield was 70% on a protein basis.

The particle size of the soy flour, ratio of enzyme to substrate, temperature, pH and time interval controls the end of enzymatic hydrolysis resulting in minimal bitterness of the hydrolysate.

The soy protein hydrolysate obtained has creamy color and an yield of 60–67.0% (on protein basis). The product has 9.4% moisture, 10.5–11.0% nitrogen and 35–45% degree of hydrolysis (TNBS procedure).

The soy protein hydrolysate obtained has 20–23 trypsin inhibitor units/mg activity (TIU), 95–98% Nitrogen Solubility Index, 0.6–1.0% of salt content (measured as Cl⁻ ions) and 2–2.2% bitterness recognition threshold. The lipoxygenase and urease activities were not detectable. The amino acid composition of the soy protein hydrolysate obtained was similar to the amino acid make up of starting raw material thereby retaining the nutritional value. The protein hydrolysate is less bitter compared to protein hydrolysate obtained from casein and is less hygroscopic in nature.

THE MAIN ADVANTAGES OF THIS INVENTION ARE

The process provides protein hydrolysate with specified degree of DH and 10.5 to 11.0% nitrogen content in a powder form.

1. By using this process, the product attains a property of being a good additive without imparting any undesirable odd flavour to the finished product.
2. The process yields a quality hydrolysate which has a solubility independent of pH making it a suitable additive either in acid pH or alkaline pH.
3. The Nitrogen recovery from the soy flour is 95–98% which is higher compared to any present method of commercial production.
4. The yield of protein hydrolyste is 65–70% of the soy bean protein.
5. The time of hydrolysis is 2 ½ to 4 h. which is short having advantage both in input cost and energy. The combination of the two enzymes is such that salt concentration will be minimal at 0.6 to 1%.
6. The enzyme employed is a food grade commercially available acceptable plant enzyme/fungal enzyme with broad specificity.
7. The nutritive value of starting material is preserved with minimum loss of essential amino acids.
8. The protein hydrolysate so obtained contained acceptable levels of trypsin inhibitor activity, free from lipoxygenase activity and urease activity and NSI is 98%.

The invention claimed is:

1. A process for the preparation of protein hydrolysates from defatted soy flour, said process comprising the steps of:
   (i) preparing an aqueous slurry of defatted soy flour having 6–12% w/v of solid content;
   (ii) subjecting said slurry to a first hydrolyzation using a fungal protease at pH 7–8 and temperature 43+5° C. for 1 to 3 hours to get 20–40% degree of hydrolysis (DH);
   (iii) subject the slurry obtained in step (ii) to a second hydrolyzation using papain at temperature 53+5° C. for −0.5 to 1.5 hours under stirring until 30–45% DH is obtained;
   (iv) inactivating residual enzymes in a known manner; and
   (v) separating solids and drying clarified supernatant thus obtained to get protein hydrolysates,
   wherein the resulting protein hydrolysates exhibit about 10.5–11.0% nitrogen content, about 20–23 trypsin inhibitor units/mg protein, a nitrogen solubility index of about 95–98%, about 35–45% of hydrolysis, and a threshold perception of bitterness greater than 2 g %, said resulting protein hydrolysates have solubility characteristics that are independent of pH, thus rendering the hydrolysates suitable additives in either acid pH or alkaline pH.

2. A process as claimed in claim 1, wherein the solid content in the slurry ranges from 8–12% w/v.

3. A process as claimed in claim 1, wherein the fungal protease is obtained from *Aspergillus* sp.

4. A process as claimed in claim 1, wherein the *Aspergillus* is selected from the group comprising of *Aspergillus flavus, Aspergillus japanicus, Aspergillus niger* and *Aspergillus awamori*.

5. A process as claimed in claim 1, wherein the fungal protease ranges from 0.4 to 0.5% w/w of the soy flour.

6. A process as claimed in claim 1, wherein the protease hydrolysis is carried out at a pH of 7.2 to 7.6.

7. A process as claimed in claim 1, wherein the amount of papain ranges from 0.4 to 0.5% w/w of the soy flour.

8. A process as claimed in claim 1, wherein the hydrolysate produced has decreased bitterness.

9. A process as claimed in claim 1, wherein the protein hydrolysate produced has low mineral content.

10. A process as claimed in claim 1, wherein protein hydrolysate obtained has creamy color and a yield of 60–67.0% (on protein basis).

11. A process as claimed in claim 1, wherein protein hydrolysate has 9.4% moisture.

12. A process as claimed in claim 1, wherein the protein hydrolysate obtained has 0.6 to 1.0% of salt content and 2 to 2.2% bitterness recognition threshold.

13. A process as claimed in claim 1, wherein lipoxygenase and urease activities of the protein hydrolysate were not detectable.

14. A process as claimed in claim 1, wherein the amino acid composition of the protein hydrolysate was similar to the amino acid makeup of the defatted soy flour in step (i).

* * * * *